US008894958B2

(12) United States Patent  
Bujoli et al.

(10) Patent No.: US 8,894,958 B2
(45) Date of Patent: Nov. 25, 2014

(54) GALLIATED CALCIUM PHOSPHATE BIOMATERIALS

(75) Inventors: Bruno Bujoli, Suce sur Erdre (FR); Jean-Michel Bouler, Carquefou (FR); Pascal Janvier, Nantes (FR); Ibrahim Khairoun, Nantes (FR); Verena Schnitzler, Nantes (FR); Charlotte Mellier, Le Loroux Bottereau (FR)

(73) Assignees: Centre National de la Recherche Scientifique (C.N.R.S.), Paris (FR); University de Nantes, Nantes (FR); Graftys, Aix-en-Provence (FR)

( * ) Notice: Subject to any disclaimer, the term of this patent is extended or adjusted under 35 U.S.C. 154(b) by 1066 days.

(21) Appl. No.: 12/716,850

(22) Filed: Mar. 3, 2010

(65) Prior Publication Data

US 2010/0248191 A1    Sep. 30, 2010

Related U.S. Application Data (60) Provisional application No. 61/157,039, filed on Mar. 3, 2009.

(51) Int. Cl.
    *C01B 15/16*    (2006.01)
    *C01B 25/26*    (2006.01)
    (Continued)

(52) U.S. Cl.
    CPC ......... *A61L 27/12* (2013.01); *C04B 2103/0021* (2013.01); *C04B 2111/00836* (2013.01); *C04B 28/34* (2013.01)
    USPC .............................. 423/306; 106/35; 106/690

(58) Field of Classification Search
    USPC .............................. 106/35, 306, 690; 423/306
    See application file for complete search history.

(56) References Cited

U.S. PATENT DOCUMENTS 4,529,593 A    7/1985 Warrell, Jr. et al.
(Continued)

FOREIGN PATENT DOCUMENTS

EP    0416761    3/1991
EP    0543765    5/1993
(Continued)

OTHER PUBLICATIONS

Matsuya et al; Effect of powder grinding on hydroxyapatite formation in a polymeric calcium phosphate cement prepared from tetracalcium phosphate and poly(methyl vinyl ether-maleic acid);Biomaterials 20 (1999) 691-697.*
(Continued)

*Primary Examiner* — Shuangyi Abu Ali
(74) *Attorney, Agent, or Firm* — Michael Best & Friedrich LLP

(57) ABSTRACT

The present invention relates to a galliated calcium-phosphate biomaterial comprising a gallium-doped phosphocalcic compound of formula (I):

$$Ca_{(10.5-1.5x)}Ga_x(PO_4)_7 \quad (I)$$

wherein 0<x<1 and the salts, hydrates and mixtures thereof and/or a calcium deficient apatite structure with in particular a (Ca+Ga)/P molar ratio in the range of 1.3 to 1.67, and a gallium content up to 4.5% by weight.
It also relates to processes of preparation of such materials and uses thereof, in particular as dental or bony implants.
It further relates to a kit comprising a galliated calcium-phosphate biomaterial in combination with a fluid component.
It finally relates to methods of use of the galliated calcium-phosphate biomaterial, notably for III) ions increase radio-opacity after bone implantation and can be released for inhibiting bone resorption.

15 Claims, 4 Drawing Sheets

(51) Int. Cl.
| | |
|---|---|
| C09K 3/00 | (2006.01) |
| C04B 12/02 | (2006.01) |
| C04B 28/34 | (2006.01) |
| A61L 27/12 | (2006.01) |
| C04B 103/00 | (2006.01) |
| C04B 111/00 | (2006.01) |

(56) References Cited

U.S. PATENT DOCUMENTS

| | | |
|---|---|---|
| 4,880,610 A | 11/1989 | Constantz |
| 5,053,212 A | 10/1991 | Constantz et al. |
| 5,690,908 A | 11/1997 | Deutsch et al. |
| 2010/0248191 A1 | 9/2010 | Bujoli et al. |
| 2010/0269734 A1 | 10/2010 | Bujoli et al. |
| 2014/0087004 A1 | 3/2014 | Bujoli et al. |

FOREIGN PATENT DOCUMENTS

| | | |
|---|---|---|
| EP | 0664133 | 7/1995 |
| FR | 2715853 | 8/1995 |
| WO | WO 96/36562 | 11/1996 |
| WO | 01/49327 | 7/2001 |
| WO | WO 2004/000374 | 12/2003 |
| WO | WO 2008/023254 | 2/2008 |

OTHER PUBLICATIONS

Blumenthal et al ;Effect of Gallium on the in Vitro Formation, Growth, and Solubility of Hydroxyapatite; CalcifTissue Int (1989) 45:81-87.*

Okamoto et al. ;Studies on calcium hosphate precipitation: Effects of metal ions used in 2p ental materials;Journal of Biomedical Materials Research, vol. 28, 1403-1410 (1994).*

Berthon et al, "Speciation Studies in Relation to the Bioavailability and Drug Activity of Tetracyclines", Handbook of Metal-Ligand Interactions in Biological Fluids, Bioinorganic Medicine, pp. 1252-1265, vol. 2, Part Five, Chapter 3, Section F, Marcel Dekker, New York. USA, 1995.

International Search Report and Written Opinion for PCT/EP2010/052723 dated May 3, 2010 (11 pages).

United States Patent Office Action for U.S. Appl. No. 13/255,069 dated Aug. 23, 2012 (9 pages).

United States Patent Office Action for U.S. Appl. No. 12/716,862 dated Aug. 14, 2012 (10 pages).

Okamoto et al, "Studies on calcium phosphate precipitation: Effects of metal ions used in dental materials", Journ. Bio. Matl. Res., vol. 28, 1994, pp. 1403-1410.

Tung et al, "An Intermediate State in Hydrolysis of Amorphous Calcium Phosphate", Calcif Tissue Int, 35, 1983, pp. 783-790.

Yang et al., "The design of scaffolds for use in tissue engineering. Part I. Traditional factors," Tissue Eng. (2001) 7(6):679-689.

Yashima, M. et al., J. Solid State Chem. (2003) 175:272.

Albee, F.H., "Studies in Bone Growth" Ann. Surg. (1920) 71:32-39.

Bernstein, L.R. , "Mechanism of Therapeutic Activity for Gallium" Pharmacological Reviews (1998) 50(4):665-682.

Blumenthal, N.C. et al., "The Effect of Aluminum and Gallium Ions on the Mineralization Process" Bull. Hosp. Jt. Dis. Orthop. Inst. (1989) 49:192-204.

Bockman, R.S. et al., "Treatment of Paget's Disease of Bone With Low-Dose, Subcutaneous Gallium Nitrate" J. Bone Miner. Res. (1989) 4:S167.

Bockman, R.S. et al., "Treatment of Patients With Advanced Paget's Disease of Bone With Two Cycles of Gallium Nitrate" J. Clin. Endocrinol. Metab. (1995) 80:595-602.

Bockman, R.S. et al., "A Multicenter Trial of Low Dose Gallium Nitrate in Patients with Advanced Paget's Disease of Bone" Semin. Arthritis Rheum (1994) 23:268-269.

Brown, W.E. et al., "A new calcium phosphate setting cement" J. Dent. Res. (1983) 62:672.

Dickens, B. et al., "Crystallographic Studies of the Role of Mg as a Stabilizing Impurity in beta-Ca3(PO4)2 I. The Crystal Structure of Pure beta-Ca3(PO4)2" J. Solid State Chem. (1974) 10:232.

Donnelly, R. et al., "The Effect of Gallium on Seeded Hydroxyapatite Growth" Calcif. Tissue Int. (1989) 44:138-142.

Donnelly, R. et al., "The Effect of Gallium Nitrate on Healing of Vitamin D- and Phosphate-Deficient Rickets in the Immature Rat" Calcif. Tissue Int. (1993) 53(6):400-410.

Dudley, H.C. et al., "Deposition of Radio Gallium (Ga72) In Skeletal Tissues" J. Pharmacol. Exp. Ther. (1949) 96:224-227.

Golubev et al., "On Double Phosphates Ca9M(PO4)7 (M=Al, Fe, Cr, Ga, Sc, Sb, In)" Neorganicheskoi khimii (1990) 35(12):3037-3041.

Jarcho, M., "Biomaterial Aspects of Calcium Phosphates—Properties and Applications" Dental Clinics of North America (1986) 30(1):25-47.

Korbas et al., "Bone tissue incorporates in vitro gallium with a local structure similar to gallium-doped brushite" J. Biol. Inorg. Chem. (2004) 9:67-76.

LeGeros et al., "Apatitic Calcium Phosphates: Possible Dental Material Restorative Materials" J. Dent. Res. (1982) Spec. Issue 61:343.

Mathew, M. et al., "The Crystal Structure of a-Ca3(PO4)2*" Acta Crystallogr. (1977) B33:1325.

Nelson, B. et al., "Distribution of Gallium Human Tissues After Intravenous Administration" J. Nucl. Med. (1972) 13:92-100.

Nery, E.B. et al., "Bioceramic Implants in Surgically Produced Infrabony Defects" J. Periodontol. (1975) 46:328-347.

Pompe, W. et al., "Functionally graded materials for biomedical applications" Matl. Sci. Eng. (2003) A362:40-60.

Ray, R.D. et al., "A Preliminary Report on Studies of Basic Calcium Phosphate in Bone Replacement" Surg. Form. (1951) 429:434.

Valappil, S.P. et al., "Controlled delivery of antimicrobial gallium ions from phosphate-based glasses" Acta Biomaterialia (2008) doi:10.1016/j.actbio.2008.09.019.

Warrell, R.P. et al., "Gallium Nitrate Inhibits Calcium Resorption from Bone and Is Effective Treatment for Cancer-related Hypercalcemia" J. Clin. Invest. (1984) 73:1487-1490.

Warrell, R.P. Jr. et al., "Metabolic Effects of Gallium Nitrate Administered by Prolonged Infusion" Cancer Treat. Rep. (1985) 69:653-655.

Warrell, R.P. Jr. et al., "Gallium in the Treatment of Hypercalcemia and Bone Metastasis" in Important Advances in Oncology, DeVita, V.T. et al. eds., J.B. Lippincott, Philadelphia, PA (1989) 205-220.

Warrell, R.P. Jr. et al., "Gallium Nitrate Inhibits Accelerated Bone Turnover in Patients With Bone Metastases" J. Clin. Oncol. (1987) 5:292-298.

Warrell, R.P. Jr. et al., "Low-Dose Gallium Nitrate for Prevention of Osteolysis in Myeloma: Results of a Pilot Randomized Study" J. Clin. Oncol. (1993) 11:2443-2450.

Warrell, R.P. Jr. " Gallium for Treatment of Bone Diseases" in Handbook of Metal-Ligan Interactions in Biological Fluids, Bioinorganic Medicine, Berthon, G. editor, Marcel Dekker, New York (1995) 2:1253-1265.

Yashima, M. et al., "Crystal structure analysis of beta-tricalcium phosphate CA3(PO4)2 by neutron powder diffraction" J. Solid State Chem. (2003) 175:272.

United States Patent Office Action for U.S. Appl. No. 12/716,862 dated Aug. 14, 2012 (12 pages).

Okamoto et al, "Studies on calcium phoshate precipitation: Effects of nmetal ions used in dental materials", Joun. Biomatl. res., vol. 28, 1994, pp. 1403-1410.

Tung et al, "An Intermediate State in Hydrolysis of Amorphous Calciu Phsphate", Calcif Tissue lnt, 35, 1983, pp. 783-790.

United States Patent Office Final Rejection for U.S. Appl. No. 12/716,862 dated Mar. 19, 2013 (8 pages).

United States Patent Office Action for U.S. Appl. No. 14/094,314 dated Jan. 16, 2014 (7 pages).

United States Patent Office Notice of Allowance for U.S. Appl. No. 14/094,314 dated Aug. 18, 2014 (6 pages).

* cited by examiner

(ppm)

*FIG.4*

GALLIATED CALCIUM PHOSPHATE BIOMATERIALS

CROSS-REFERENCE TO RELATED APPLICATIONS

This application claims the benefit of priority to U.S. Provisional Application No. 61/157,039 filed Mar. 3, 2009, the entire disclosure of which is herein incorporated by reference in its entirety for any purpose.

FIELD OF THE INVENTION

The invention relates to galliated calcium phosphate biomaterials such as calcium phosphate cements, to methods of manufacture and methods of use thereof.

BACKGROUND OF THE INVENTION

Deregulation of the bone activity of an individual is the cause of many bone pathologies such as osteoporosis, Paget's disease or osteolytic tumors. Taking into account, in particular, the increase in human life expectancy, osteoporosis has become a public health problem and much research has been undertaken to remedy it. Since the bone pathologies under consideration are caused by an imbalance in bone remodeling to the benefit of the activity of osteoclasts, one of the routes of treatment envisioned consisted in reducing the activity of osteoclasts, in order to slow down the degradation of the bone material.

Bone is a composite of biopolymers, principally collagen, and an inorganic component identified as carbonate hydroxyapatite, approximated as $(Ca,Mg,Na,M)_{10}(PO_4, CO_3,HPO_4)_6(OH,CO_2)$.

The concept and potential advantages of synthetic calcium phosphate materials as possible restorative material was first introduced at the beginning of the $20^{th}$ century (Albee 1920, Ray and Ward 1951, Nery et Al., 1975). Apatitic or calcium phosphate cement (CPC) as a possible restorative material was first introduced by LeGeros et al. in 1982 and Brown & Chow in 1983.

There are presently a number of calcium phosphate materials on the market, in the form of powders, granules, mixtures with biocompatible polymers, implants, thin coatings or calcium phosphate cements (CPC).

The most widely used compounds are hydroxyapatite (HA, $Ca_{10}(PO_4)_6(OH)_2$) and tricalcium phosphate (TCP, $Ca_3(PO_4)_2$). TCP has been shown to resorb rather quickly, but HA has advantages due to its chemical and physical properties similar to biological apatite crystals. A combination of TCP and HA, called biphasic calcium phosphate (BCP), provides a combination of these desirable properties (see Legeros R. et al. 2003).

Calcium phosphate bioceramics may be prepared by precipitation of powders from aqueous solutions of the starting chemicals. These powders are compacted under high pressure (between 100 and 500 MPa) and then sintered at a temperature between 1000° C. and 1300° C. (See Jarcho, 1986).

Biphasic calcium phosphate (BCP) may be obtained when calcium-deficient biologic or synthetic apatites are sintered at or above 700° C. An apatite is considered calcium deficient when the Ca/P ratio is less than the stoechiometric value of 1.67 for pure calcium hydroxyapatite.

Polymer-ceramic composites and polymer networks have been developed to provide suitable porosity, however generally at the expense of desirable mechanical properties (see Yang et al., 2001; Pompe W. et al. 2003).

To date, a wide variety of implant materials have been used to repair, restore, and augment bone. The most commonly used implants include autologous bone, synthetic polymers and inert metals. Protocols using these materials have significant disadvantages that can include patient pain, risk of infection during operations, lack of biocompatibility, cost, and the risk that the inserted hardware can further damage the bone. Therefore, a major goal of biomaterial scientists has been to develop novel bone substitutes that can be used as alternatives to these conventional techniques for skeletal repair.

Bone cements, such as cements based on polymethylmethacrylate (PMMA) offer certain advantages in avoiding the use of solid implants, but also have several disadvantages. Methacrylates and methacrylic acid are known irritants to living tissues, and when PMMA-based cements are cured in vivo, free radicals are generated, which can damage surrounding tissues. Moreover, the polymerization reaction for these materials is highly exothermic, and the heat evolved during curing can damage tissues. In addition, these materials are not biodegradable.

The concept and potential advantages of an apatitic or calcium phosphate cement (CPC) as a possible restorative material was first introduced by LeGeros et al in 1982 ("Apatitic Calcium Phosphates: Possible Restorative Materials", J Dent Res 61(Spec Iss):343).

There are presently several CPC commercial products. CPC have the following advantage: malleability allowing them to adapt to the defect's site and shape. The introduction of injectable calcium phosphate cements greatly improved the handling and delivery of the cements and opened up areas of new applications for the CPC.

CPC systems consist of a powder and a liquid component. The powder component is usually made up of one or more calcium phosphate compounds with or without additional calcium salts. Other additives are included in small amounts to adjust setting times, increase injectability, reduce cohesion or swelling time, and/or introduce macroporosity.

Such materials are disclosed, for example, in EP 0 416 761, U.S. Pat. No. 4,880,610, U.S. Pat. No. 5,053,212, EP 0 664 133, EP 0 543 765, WO 96/36562 and WO 2004/000374.

The French patent application FR-2715853 describes compositions for biomaterials for resorption/substitution of support tissues, comprising a mineral phase composed of BCP or calcium-titanium-phosphate, and a liquid aqueous phase comprising an aqueous solution of a cellulose-based polymer. These injectable compositions contain no active principle.

Many studies have shown that gallium inhibits bone resorption and lowers plasma calcium through its antiresorptive activity (e.g., Warrell et al., 1984, 1985; Warrell and Bockman, 1989; Bernstein, L. R. 1998). For example, U.S. Pat. No. 4,529,593 discloses a method effective against excessive loss of calcium from bone using a gallium compound, such as gallium nitrate. The excessive loss of calcium may be linked to hypocalcaemia, osteoporosis or hyperparathyroidism. The gallium compound is administered intravenously, subcutaneously or intramuscularly.

Based on its antiresorptive activity, gallium has also been used in the clinical treatment of hypocalcaemia of malignancy (Warrell and Bockman, 1989) and Paget's disease of bone (Bockman and Bosco, 1994; Bockman et al., 1989, 1995). Gallium has also shown clinical efficiency in suppressing osteolysis and bone pain associated with multiple myeloma and bone metastases (Warrell et al., 1987, 1993), and has been suggested as a treatment for osteoporosis (Warrell, 1995). In vitro efficiency as antibacterial agent has also been reported (Valappil, 2008).

Gallium has long been known to concentrate in skeletal tissue, particularly regions of bone deposition and remodeling (e.g., Dudley and Maddox, 1949; Nelson et al., 1972). However, very little information exists on mechanisms of gallium uptake by bone cells and the mechanisms of skeletal gallium accumulation remain largely unknown. Gallium is known to adsorb in vitro to synthetic hydroxyapatite and as a result crystallization and probably dissolution of hydroxyapatite is decreased (Donnelly and Boskey, 1989; Blumenthal and Cosma, 1989). In a recent study, Korbas et al., 2004, reported experiments in which bone tissue incorporates in vitro gallium with a local structure similar to brushite. The gallium doped model compounds disclosed have a Ca/P molar ratio of 1 (ACP, brushite) and 1.66 (HAP).

Gallium nitrate is currently marketed as Ganite™, which product is administered through intravenous injection for the treatment of clearly symptomatic cancer-related hypocalcaemia that has not responded to adequate hydration. According to the FDA approved labelling for Ganite™, gallium nitrate exerts a hypocalcemic effect by inhibiting calcium resorption from bone, possibly by reducing increased bone turnover. Indeed, gallium may have an inhibitory effect on osteoclasts responsible for bone resorption and an increasing effect on osteoblasts responsible for bone growing without cytotoxic effect on bone cells (Donnelly, R., et al., 1993).

The incorporation of gallium into a biomaterial such as a calcium phosphate cement is not trivial. Indeed, the pH of an apatitic calcium phosphate cement paste is close to neutral, while the gallium ions are stable in solution only at pH<3 in form of an octahedral hexa-aqua complex or at pH>8 in form of gallate ions. This results in a quick and uncontrolled precipitation of amorphous $Ga(OH)_3$ before complete setting of the cement. In addition, the gallium ions may interfere with the setting and hardening process, since gallium can trap phosphate ions resulting from the dissolution and precipitation process occurring during cement setting.

TECHNICAL PROBLEM

There is thus still a need for providing an alternative administration route for gallium, in particular for reinforcing weak bone structures where osteoclastic activity needs to be locally inhibited because of e.g. osteoporosis, Paget's disease or osteolytic tumors, in particular by way of introducing gallium into biomaterials which may be placed close to the bone sites. There is a particular interest to provide such a route which allows a precise tuning of the gallium release in terms of dosage and duration according to the therapeutic needs.

SUMMARY OF THE INVENTION

The present inventors have shown that it is possible to prepare galliated calcium phosphate biomaterials from gallium-doped phosphocalcic compounds, some of which comprising Ga(III) ions within their crystal lattice, thus limiting the potential interference of gallium with the setting reaction, due to precipitation. Further, it has been shown that such galliated calcium phosphate biomaterials are capable of releasing gallium in vivo. Finally, the use of gallium doped calcium phosphate compounds with a molar ratio Ca/P comprised between 1.28 and 1.5 allows for optimal gallium release characteristics. Indeed, highly water soluble calcium phosphate compounds such as gallium doped brushite (Ca/P=1) is expected to exhibit a rapid gallium release and thus a short activity span with a risk of overdosage while sparingly water soluble calcium phosphate compounds such as gallium doped hydroxyapatite (HAP) (Ca/P=1.66) is expected to exhibit a gallium release which may be insufficient for any therapeutic effect.

A first object of the present invention thus relates to a galliated calcium phosphate biomaterial comprising a gallium-doped phosphocalcic compound.

Such galliated calcium phosphate biomaterials include in particular self-setting calcium phosphate cement (CPC) and composite phosphocalcic-polymer cement. The cements are preferably injectable. Injectable cement may be introduced directly to the required bone site by injection, where the cement sets and may subsequently release locally gallium in situ, close to the site in need thereof, upon degradation by bone cells.

Further biomaterials include ceramic implants such as bony or dental implants manufactured from the galliated calcium phosphate biomaterial, and which may be implanted into the body subsequently.

According to a second aspect, the invention further proposes processes for the manufacture of the gallium-doped calcium phosphate biomaterials.

According to a third aspect, the invention further provides a process for the manufacture of the implants comprising a galliated calcium phosphate biomaterial.

According to a fourth aspect, the invention further provides a kit which comprises a gallium-doped calcium phosphate biomaterial in combination with a fluid phase such as a liquid or a gel.

Finally, according to a fifth aspect, the invention provides methods for reconstructive bone surgery and methods of treatment of bone diseases notably due to osteoclastic dysfunctions comprising the introduction into the body of the patient in need thereof, close to the bone site to be treated, of a galliated calcium phosphate biomaterial according to the invention.

DEFINITIONS

In the context of the present invention, the term "phosphocalcic" or "calcium phosphate" refers to minerals containing calcium ions ($Ca^{2+}$) together with orthophosphate ($PO_4^{3-}$), metaphosphate or pyrophosphate ($P_2O_7^{4-}$) and occasionally other ions such as hydroxide ions or protons.

Particular calcium phosphate compounds are tricalcium phosphate (TCP) ($Ca_3(PO_4)_2$) and allotropic forms, apatite ($Ca_5(PO_4)_3X$ with X being F, Cl, OH) and hydroxyapatite (HA), an apatite wherein the extra ion is mainly hydroxide.

Other calcium phosphate compounds are amorphous calcium phosphate (ACP), ($Ca_x(PO_4)_y.H_2O$), monocalcium phosphate monohydrate (MCPM) ($CaH_4(PO_4)_2.H_2O$), dicalcium phosphate dihydrate (DCPD) ($CaHPO_4. 2H_2O$) also called brushite, dicalcium phosphate anhydrous (DCPA) ($CaHPO_4$) also called monetite, precipitated or calcium-deficient apatite (CDA), $(Ca,Na)_{10}(PO_4,HPO_4)_6(OH)_2$ and tetracalcium phosphate (TTCP) ($Ca_4P_2O_9$) also called hilgenstockite.

The term "biocompatible" as used herein, means that the material does not elicit a substantial detrimental response in the host.

The term "bioresorbable" refers to the ability of a material to be resorbed in vivo. In the context of the present invention, "full" resorption means that no significant extracellular fragments remain. The resorption process involves elimination of the original implant materials through the action of body fluids, enzymes or cells.

Resorbed calcium phosphate may, for example, be redeposited as new bone mineral via osteoblastic cells action, or by being otherwise, reutilized within the body or excreted. "Strongly bioresorbable" means that a major part of the calcium phosphate implant is resorbed between one and five years. This delay depends not only on intrinsic features of the calcium phosphate implant but also on the implanted site, age of the patient, primary stability of implant etc. . . .

In the context of the present invention, a "calcium phosphate cement" (CPC) is a solid composite material comprising or made of one or more calcium phosphates eventually with additional calcium salts which sets and hardens in presence of water or an aqueous solution. The term CPC refers to the paste resulting from the mixing of the solid material with the water or the aqueous solution as well as to the hardened material obtained after setting. Other additives may be included in small amounts to adjust the properties of the cement such as the setting time, the viscosity, reduce cohesion or swelling time, and/or induce macroporosity, and confer elasticity to the final hardened product.

In the context of the present invention, the "setting" of a cement means the hand-off self-hardening of the cement paste at ambient temperature, that is, depending on the environment, room temperature or body temperature.

In the context of the present invention, an "injectable cement" or a "cement in a form suitable to be injected" refers to a cement paste which may be pushed through a needle with a diameter of a few millimeters, preferably between 1 and 5 mm, more preferably between 1 and 3 mm, most preferably between 2 and 3 mm. Particularly important parameters for injectable cements include the absence of large particles, a suitable viscosity as well as an appropriate setting time in vivo (at 37° C.).

The term "bioceramic" is employed to designate biocompatible ceramic materials.

The term "biomaterial" is used to designate biocompatible materials.

Galliated Calcium Phosphate Biomaterials

According to a first aspect, the invention provides a galliated calcium phosphate biomaterial comprising a gallium-doped phosphocalcic compound of formula (I):

$$Ca_{(10.5-1.5x)}Ga_x(PO_4)_7 \quad (I)$$

wherein 0<x<1
and the salts hydrates and mixtures thereof.

The salts may be in particular compounds of formula (I) wherein the calcium is partially replaced by other elements such as Zn, Cu, Mg, Na, K.

Preferably, the galliated calcium phosphate material according to the invention contains a compound of formula (I) wherein 0<x≤0.85.

Preferred gallium-doped phosphocalcic compound of formula (I) may be selected from the group consisting of $Ca_{10.125}Ga_{0.25}(PO_4)_7$; $Ca_{9.75}Ga_{0.5}(PO_4)_7$; $Ca_{9.375}Ga_{0.75}(PO_4)_7$; and $Ca_{9.27}Ga_{0.82}(PO_4)_7$.

The galliated calcium phosphate biomaterials preferably comprise a phosphocalcic compound with a β-tricalcium phosphate (β-TCP)-like structure and/or phosphocalcic compound with a calcium deficient apatite (CDA)-like structure.

In some embodiments, the galliated calcium-phosphate biomaterial may further comprise a polymer.

The gallium-doped phosphocalcic compound used preferably presents a β-tricalcium phosphate-like structure (β-TCP) (Dickens, B. et al., 1974; Yashima, M. et al., 2003). Such structure shows a R3c space group, with cell parameters varying in the following range, as a function of the Ga content: a=10.31-10.44 Å, c=37.15-37.5 Å, α=90'; β=90° and γ=120°.

While not particularly limited, the gallium content in the galliated calcium phosphate material is for most applications preferably up to 6.35% by weight, in particular 0.001 to 6.0% by weight, and most preferably 0.01 to 5.3% by weight.

Generally, at least part of the gallium is located within the crystal lattice of the gallium-doped compounds present in the galliated material, preferably at the calcium sites.

According to preferred embodiment, the invention provides a galliated calcium-phosphate biomaterial comprising a gallium-doped calcium deficient apatite (CDA), with a (Ca+Ga)/P molar ratio in the range of 1.3-1.67, and prepared by either (i) precipitation out of an aqueous solution containing gallium, calcium and phosphate ions, preferably by way of increasing the pH close to 7 (gallium content up to 4.5% by weight), or (ii) suspension of CDA in a gallium nitrate solution at controlled pH close to 8 (gallium content up to 0.65% by weight).

According to a third aspect, the invention further provides a process for the manufacture of the implants comprising a galliated calcium phosphate biomaterial comprising the step of:

(i) mixing a self-setting galliated calcium phosphate biomaterial according to the invention with an appropriate amount of an aqueous liquid phase to obtain a cement paste; and (ii) forming the cement paste into an implant.

After setting, the implant comprising a galliated calcium phosphate biomaterial prepared may be used to repair, restore, and augment bone and/or to fill bony or tooth defects.

According to a fourth aspect, the invention further provides a kit which comprises a gallium-doped calcium phosphate biomaterial in combination with a fluid phase such as a liquid or a gel.

Calcium Phosphate Cement

Preferred galliated calcium-phosphate biomaterials according to the invention are self-setting materials such as calcium-phosphate cements (CPC).

The setting time is an important property of the calcium phosphate cement. If it is too short, the surgeon does not have time to use the cement before it is hard. If the setting time is too long, the surgeon risks losing time while waiting to close the wound. The setting time depends on different parameters such as the composition of the solid and liquid phases, the solid-to-liquid ratio, the proportion of the calcium phosphate components and the particle size of the solid phase components.

The setting time is usually measured on a moulded sample with a Gillmore needle apparatus. This test basically measures when the hydrating cement paste develops some finite value of resistance to penetration. It defines an initial setting time and a final setting time based on the time at which a needle of particular size and weight either penetrates a cement paste sample to a given depth or fails to penetrate a cement paste sample. The Gillmore needle apparatus consists in two needles with a different diameter and a different weight. The first needle with the highest diameter and the lowest weight is used to measure the initial setting time and the second one with the lowest diameter and the highest weight is used to measure the final setting time (C266 ASTM standard).

Alternatively, texture analyses can be used to evaluate the open time for using the cement. The method consists in measuring versus time, the compression force necessary to extrude the cement paste until extrusion becomes impossible.

In order to be suitable for a surgical use, the initial setting time of the CPC at 37° C. is typically less than 1 hour, more preferably less than 45 min, most preferably less than 10 min, and the final setting time at 37° C. is less than 3 hours, preferably less than 40 min, most preferably less than 20 min.

Once hardened, the galliated CPC according to the invention has a high compression strength, typically above 10 MPa, preferably above 20 MPa, which makes it well compatible with the uses contemplated for this material.

The preparation of the cement paste prior to injection consists in mixing together for about 2 minutes, a selected solid phase and a selected liquid phase, in appropriate respective amounts.

In the case of apatitic cements, in aqueous solution, the main solid component is α-TCP which hydrates to yield calcium-deficient hydroxyapatite (CDA). In the case of brushite cements, the main solid component is β-TCP which is transformed into dicalcium phosphate dihydrate (DCPD), also called brushite. In each case, the reaction leads to the hardening of the composition, and allows for the preparation of self-setting calcium-phosphate cements.

Self-setting materials such as calcium phosphate cement have the advantage of malleability allowing them to adapt to the defect's site and shape, while also providing primary mechanical solidity to the implant.

A further object according to the invention is thus a galliated calcium phosphate cement comprising or consisting of the gallium-doped compound according to the invention, which are particularly interesting for the local administration of gallium in situ close to the bone sites. Preferably, the galliated calcium phosphate cement is in a form suitable to be injected.

An injectable galliated CPC is particularly useful for the repair of osteoporotic fractures. In recent years, the occurrence of osteoporotic fractures has dramatically increased. Considering the lack of adequate treatment and the increasing number of elderly people, this trend is expected to continue. The repair of osteoporotic fractures is however difficult, because the bone is very weak. It is thus generally impossible to insert screws to hold osteosynthesis plates. A way to solve the problem is to inject a CPC into the osteoporotic bone to reinforce it.

a. The Solid Phase

Before setting, the calcium phosphate cement is a finely divided composition comprising according to the invention a gallium-doped phosphocalcic compound. Preferably, the gallium-doped phosphocalcic compound is derived from β-TCP or CDA.

Further to the gallium-doped phosphocalcic compound, the solid phase of the calcium phosphate cement preferably further comprises other compounds in order to optimize its properties such as the setting behaviour, elasticity or mechanical resistance.

Preferably, the solid phase comprises calcium and/or calcium phosphate compounds such as HA, α-TCP, β-TCP, ACP, MCPM, DCPA, DCPD, CDA, $CaSO_4.2H_2O$, $CaCO_3$.

Most often, the solid phase comprises $CaHPO_4$ and one or more other phosphocalcic compounds.

Generally, the main component of the cement is α-TCP. Galliated calcium phosphate cements powders thus preferably comprise 30 to 90% by weight of α-TCP. The phosphate cements further comprise up to 50%, preferably 5 to 30% by weight of $CaHPO_4$. Further, the calcium phosphate cements may comprise up to 50%, preferably 10 to 30% by weight of β-TCP, which may be gallium doped. The calcium phosphate cements may further comprise up to 30%, preferably 1 to 15% by weight of CDA, which may be gallium doped.

For apatitic cements, the solid phase of such a CPC may comprise at least 40%, 50%, 60%, 78% or even up to 100% of α-TCP. The most preferred solid phase of a CPC according to the invention is a mixture of α-TCP (with up to 20% of the β-TCP), DCPD, MCPM, hydroxypropylmethylcellulose (HPMC) and precipitated calcium deficient hydroxyapatite (CDA). In this case, gallium is introduced in the solid phase as gallium-doped β-TCP or gallium-doped CDA.

For brushite cements, the solid phase comprising β-TCP and MCPM is more preferred. In a preferred embodiment, the solid phase of such a CPC according to the invention comprises at least 70%, 80% or even 90% of β-TCP. The most preferred solid phase consists in a mixture of β-TCP and MCPM. In this case, gallium is introduced in the solid phase as gallium-doped β-TCP.

The solid phase of the galliated calcium phosphate cement according to the invention can further include an organic component such as one or more biocompatible and bioresorbable polymers. Such polymers may be chosen in particular from polyacids, polyesters and polysaccharides. Particularly useful are polylactic acids, polyglycolic acids, poly($\epsilon$)caprolactones, polyphosphazenes, dendrimers and polysaccharides, polyorthoesters, polyanhydrides, polydioxanones, hyaluronic acid, polyhydroxyalkanoates and polyhydroxybutyrates as well as salts, copolymers, blends and mixtures thereof.

Polyphosphazenes, dendrimers, polysaccharides, poly($\epsilon$) caprolactones, polyesters, polyhydroxyalkanoates and their salts and mixtures thereof are preferred. In addition to their physical and mechanical properties, they can be produced with appropriate resorption speed, hydrophilic properties and solubility. Upon dissolution, connected micropores are created within the cement, which allows for a control of the resorbability and guided resorption-substitution of the galliated material.

Polyphosphazenes are preferably selected from the group consisting of poly(ethyloxybenzoate)phosphazene (PN-EOB), poly(propyloxybenzoate) phosphazene (PN—POB), poly[bis(sodium carboxylatophenoxy)phosphazene] (Na—PCPP), poly[bis(potassium carboxylatophenoxy)phosphazene] (K—PCPP), poly[bis(ethylalanato) phosphazene] (PAIaP), poly[bis(carboxylatophenoxy)phosphazene] (acid-PCPP), and their salts and mixtures thereof.

Polysaccharides are the most preferred polymers, in particular cellulose ethers, such as hydroxypropylmethylcellulose (HPMC) and carboxymethylcellulose (CMC).

The biocompatible and bioresorbable polymers can be used as fine powders, fibers or microparticles.

In such compositions, the inorganic component allows for an intimate bond with the native bone and osteogenic properties while the organic component allows for an interconnected macroporosity in the mineral matrix and improves the cohesion, the elasticity, the rheological properties and the injectability of the cement.

If present, the organic component of the galliated calcium phosphate cement generally varies between 0.1 and 30%, preferably 0.2 to 5% by weight and more preferably 0.5 and 3%, and in particular 1 and 2% by weight of the solid phase.

The galliated calcium phosphate cements according to the invention may be prepared according to conventional methods known in the art, such as the one disclosed in the international application WO2008023254.

Generally, the components of the cement powder are finely ground before or after mixing. As an example, the components may be ground so that about 50% by weight of the solid had a particle size between 0.1 and 8 μm, about 25% by weight of the solid had a particle size between 8 and 25 μm and a further 25% by weight of the solid had a particle size between 25 and 80 μm.

A self setting galliated calcium phosphate biomaterial may be manufactured according to a process comprising the steps of:

providing an appropriate amount of optionally galliated TCP ($Ca_3(PO_4)_2$);

mixing the TCP with appropriate amounts of one or more gallium doped phosphocalcic compounds and optionally other additives; and grinding of the components to form a solid phase of a calcium phosphate cement.

b. The Liquid Phase

The liquid phase used for the setting of the calcium phosphate cement is preferably water, or aqueous solutions of compounds such as salts, polymers, pH regulating agents such as acids, or pharmaceutically active principles such as those listed in Table I.

TABLE I compounds suitable to be included in the liquid phase of CPC

| Component | Compounds |
| --- | --- |
| Sodium | NaF, NaCl, $Na_2CO_3$, $NaHCO_3$, $Na_2SO_4$, $Na_2SiO_3$, Na orthophosphates |
| Potassium | KF, $K_2CO_3$, $K_2SO_4$, KCl, $K_2SiO_3$, K orthophosphates |
| Magnesium | $MgHPO_4$, $Mg_3(PO_4)_2 \cdot xH_2O$, $MgF_2$, $MgCO_3$, MgO, $CaMg(CO_3)_2$, $Mg(OH)_2$ |
| Zinc | $Zn_3(PO_4)_2 \cdot xH_2O$, $ZnF_2$, $ZnCO_3$, $ZnSO_4$, ZnO, $Zn(OH)_2$, $ZnCl_2$ |
| Calcium | $Ca_5(PO_4)_3OH$, $CaSO_4$, $CaSO_4 \cdot \frac{1}{2}H_2O$, $CaSO_4 \cdot 2H_2O$, $CaF_2$, $CaCO_3$, $CaCl_2$ |
| Biopolymers | Proteins, peptides, proteoglycans, glycosaminoglycans, carbohydrates, polyhydroxyalkanoates |
| Organic acids | Citric acid, malonic acid, pyruvic acid, tartaric acid |
| Inorganic acids | Phosphoric acid |
| Synthetic polymers | Polylactic acid, polyglycolic acid |
| Growth factors | TGF-β, osteocalcine, GLA proteins |

In most cases, the liquid phase contains low concentrations of the cited compounds. Typically, it contains 0.001% to 5% by weight, preferably 0.01 to 3% by weight, and most preferably 0.1 to 1% by weight of the cited compounds, with respect to the weight of the final liquid phase.

The pH of the liquid phase should preferably be adjusted to be between 5 to 10, preferably between 5 and 9, most preferably between 5 and 7.

For apatitic calcium phosphate cements, a preferred liquid phase consists in a $Na_2HPO_4$ aqueous solution, a $NaH_2PO_4$ aqueous solution or a citric acid solution. More preferably, the liquid phase consists in a $Na_2HPO_4$ aqueous solution. For example, a solution of about 0.5% to about 5% by weight of $Na_2HPO_4$ in distilled water, a solution of about 0.5% to about 5% by weight of $NaH_2PO_4$ in distilled water or a solution of about 0.5% to about 5% by weight of citric acid in distilled water can be used.

For brushite calcium phosphate cements, a preferred liquid phase is $H_3PO_4$ aqueous solution. The solution contains generally from 0.25 to 3.0 mol $L^{-1}$ of the mentioned compound, the most preferably 3.0 mol $L^{-1}$.

The ratio between liquid phase and solid phase of the calcium phosphate cement may largely vary, in particular in view of the parameters such as viscosity and setting time required for the envisaged application. Typically, the liquid phase/solid phase (L/S) ratio of the CPC is between 0.2 to 0.9 ml/g, preferably between 0.3 to 0.8 ml/g, still preferably between 0.25 to 0.5 ml/g.

If water is the liquid phase, the liquid phase/solid phase (L/S) ratio is preferably between about 0.20 to about 0.9 ml/g, more preferably between about 0.25 to about 0.8 ml/g, still preferably between about 0.25 to about 0.45 ml/g, the most preferably about 0.30 to about 0.45 ml/g.

If the liquid phase is an aqueous solution of $Na_2HPO_4$ or $NaH_2PO_4$, the liquid phase/solid phase (L/S) ratio is preferably between about 0.25 ml/g and about 0.9 ml/g; more preferably between about 0.30 ml/g and about 0.45 ml/g.

If the liquid phase is an aqueous citric acid solution, the liquid phase/solid phase (L/S) ratio is preferably between about 0.20 ml/g and about 0.8 ml/g; more preferably between about 0.25 ml/g and about 0.30 ml/g.

The calcium phosphate cements may be brought in form by usual methods known in the art.

Bioceramics

According to another embodiment, the galliated calcium phosphate biomaterial according to the invention comprises or consists of a bioceramic, which can be used as bioresorbable and osteoconductive bone graft substitute and for the manufacture of implants.

Preferably, said bioceramic comprises or consists of one or more sintered calcium phosphate compounds selected from the group consisting of β-tricalcium phosphate (β-TCP) and hydroxyapatite (HA), at least one of them being gallium-doped. Such bioceramics may be manufactured in the form of granules or agglomerated granules, or in form of cones, cylinders and sticks.

Particularly interesting is the use of bioceramics in form of granules embedded into a gel. For such an application, granules are preferably between 40 and 5000 μm, more preferably 40 to 80 μm in size.

Gallium Doped Phosphocalcic Compounds and their Preparation

The gallium-doped phosphocalcic compound of formula (I) included in biomaterials according to the invention:

$$Ca_{(10.5-1.5x)}Ga_x(PO_4)_7 \qquad (I)$$

wherein $0<x<1$, preferably $0<x\leq0.85$ and in particular $0<x\leq0.82$ and the salts hydrates and mixtures thereof may be obtained using the processes described hereafter.

The gallium doping and the presence of the phosphocalcic support can be evidenced by powder X-ray diffraction and $^{31}P$ and $^{71}Ga$ solid state NMR, the two latter methods showing both. Indeed, replacement of calcium by gallium results in an upfield shift of the $^{31}P$ NMR lines related to the phosphate groups bound to gallium, while the coordination geometry of gallium can be obtained from the $^{71}Ga$ chemical shift value.

Without wishing to be bound to any theory, the inventors have shown that the gallium ions are at least partially incorporated into the phosphocalcic compound by replacement of Ca(II) ions by Ga(III) ions in the crystal lattice and creation of vacancies to compensate for the difference in cation charge. Because the ionic radius of Ga(III) ions is smaller than that of Ca(II) ions, the replacement reaction is expected to lead to the contraction of the unit cell. The gallium-doped compounds are thus likely to present a deformed structure.

The preferred gallium-doped phosphocalcic compounds are based on the β-TCP or CDA structures.

The gallium-doped phosphocalcic compound may be totally or partially amorphous, but it is preferably at least partially crystalline. In particular, the phosphocalcic compound may contain one or more crystalline phases.

The crystalline phases of the gallium-doped phosphocalcic compounds may be in particular related to β-tricalcium phosphate (β-TCP) (Dickens, B. et al., 1974; Yashima, M. et al., 2003).

Tricalcium phosphate (TCP) has the formula $Ca_3(PO_4)_2$ and is also known as calcium orthophosphate, tertiary calcium phosphate tribasic calcium phosphate or bone ash. The β-TCP form crystallises in the space group R3c and has the following cell parameters: a=10.435 Å, c=37.403 Å, α=90°; β=90° and γ=120°.

The gallium is preferably included in the crystal lattice of the phosphocalcic compound. In this case, it is particularly preferred that the gallium ions occupy the calcium sites.

However, it has been observed that gallium-doped phosphocalcic compounds obtained at low temperature may comprise gallium species adsorbed at the surface. Heating such compounds generally leads to the diffusion of the gallium into the crystal structure.

Two different processes for the manufacture of the above gallium-doped phosphocalcic compounds are described hereafter, a solid-state process and a process in solution.

The first process is a solid-state process and comprises the steps of:
  (a) contacting calcium phosphate with calcium carbonate in presence of a suitable quantity of a gallium compound;
  (b) sintering the mixture to form a gallium-doped phosphocalcic compound; and
  (c) recovering the gallium-doped phosphocalcic compound.

Compounds thus prepared may have a gallium content of up to 5.3% by weight.

The process is preferably carried out in absence of water. Therefore, the use of dicalcium phosphate such as DCPA or DCPD or a mixture thereof is preferred. For the same reason, the reactants are preferably anhydrous compounds.

The calcium carbonate is decomposed to yield carbon dioxide and thus limiting contamination of the sample with undesired anions.

Preferred gallium compounds of use in step (a) of the process are chosen among those that are non volatile and stable at ambient conditions, and include in particular gallium oxide and precursors transformed into oxides during sintering such as gallium hydroxide.

In case the gallium is incorporated in form of its oxide, the reaction can be represented by the following equation:

$$7CaHPO_4 + (3.5-1.5x)CaCO_3 + (x/2)Ga_2O_3 \rightarrow Ca_{10.5-1.5x}Ga_x(PO_4)_7 + 3.5H_2O + (3.5-1.5x)CO_2$$

with 0<x<1

The process is preferably conducted using stoechiometric quantities of the reactants.

The temperature at step (b) is chosen preferably to be close or above the fusion temperature of the reactants. Generally, a temperature of 750° C. to 1570° C., preferably 800° C. to 1550° C., in particular 900° C. and 1360° C. and in particular 1000° C. is appropriate.

Preferably, step (b) is carried out until complete sintering, typically during a period of time of more than 12 hours, more preferably of 24 hours or more. It may be advantageous to ground the resulting solid and perform an additional calcination. This process can be repeated several times.

Gallium-doped phosphocalcic compounds are obtainable according to the above solid-state process.

The process will yield the modified phosphocalcic compound in the crystal form which is formed under the process conditions. More specifically, the process described will yield gallium-doped phosphocalcic compound with a structure close to βTCP. Such structure shows a R3c space group, with cell parameters varying in the following range, as a function of the Ga content: a=10.31-10.44 Å, c=37.15-37.5 Å, α=90°; β=90° and γ=120°.

Another process for the manufacture of gallium-doped phosphocalcic compounds proposed is conducted in solution.

The process provides gallium-doped phosphocalcic compounds as described by precipitation out of an aqueous solution containing gallium, calcium and phosphate ions, preferably by way of lowering the pH.

More specifically, the process in solution for the manufacture of a gallium-doped compound comprises the steps consisting of:
  (a) preparing an aqueous solution containing a calcium compound and an appropriate quantity of a gallium compound;
  (b) adjusting the pH of the solution obtained in step (a) to a value of 8.5 to 12, preferably 9 to 11, more preferably 9 to 9.5, if necessary;
  (c) adding to said solution an appropriate quantity of a phosphate compound;
  (d) precipitating a gallium-doped phosphocalcic compound by adjusting the pH of said solution to a value of 7.0 to 12, preferably 7.5 to 9, more preferably 7.5 to 8; and
  (e) separating the precipitated gallium-doped phosphocalcic compound from the solution.

Compounds thus prepared may have a gallium content of up to 0.65% by weight and generally have a (Ca+Ga)/P molar ratio in the range of 1.3 to 1.67.

The calcium and gallium compounds used to prepare the solution in step (a) may be chosen from a wide variety of water soluble compounds such as salts or complexes.

Preferably, said gallium compound in step (a) is selected from the group consisting of gallium acetate, gallium carbonate, gallium citrate, gallium chloride, gallium bromide, gallium iodide, gallium fluoride, gallium formate, gallium nitrate, gallium oxalate, gallium sulfate, a gallium oxide or hydroxide, and their hydrates. Particularly preferred is gallium nitrate, in view of its high solubility.

Preferably, the calcium compound is selected from the group consisting of calcium nitrate, calcium acetate, calcium chloride and calcium fluoride, and their hydrates. As for the gallium compound, calcium nitrate, and especially calcium nitrate tetrahydrate, is particularly preferred because of its high solubility.

In order to enhance purity of the prepared compound, it is preferred to use ultrapure water to prepare the solutions used in the process. "Ultrapure water" means water having a resistivity of at least 18 MΩcm.

Step (b) is conveniently carried out by adding a pH adjusting agent such as a base or an acid. Preferred are strong bases and acids which do not introduce further ions. An appropriate pH adjusting agent is an ammonia solution.

The phosphate compound used in step (c) may be any soluble salt or complex containing the phosphate anion of the gallium-doped compound envisaged.

Such a salt may be conveniently a hydrogen phosphate salt. Most preferably, the cation is volatile, for example ammonium, in order to avoid any contamination of the compound by replacement of calcium with other cations and thus ensure a high purity of the compound. Preferably, the phosphate may also be used. Advantageously, the salt is previously dissolved in water.

During step (c), the solution turns white upon the starting of the precipitation of the gallium-doped phosphocalcic compound.

In order to ensure a homogeneous concentration of the reactants, the reaction mixture is preferably stirred during step (c) and (d). For step (d), the reaction mixture is preferably stirred at about 50° C. for at least 30 minutes.

The molar ratio of the reactants is preferably stoechiometric and thus depends mainly on the ratio (Ca+Ga)/P required.

In order to speed up the reaction, the precipitation in step (d) is preferably carried out at elevated temperature between 20 and 100° C., more preferably between 40 and 80° C., the most preferably at 50° C.

The pH adjusting agent used in step (d) is again preferably a compound which does not add any further ions to the reaction mixture. Particularly preferred is an ammonia solution.

The reaction proceeds smoothly within minutes or hours. Preferably, the step (d) is carried out for a period of time between 15 min and 72 h, more preferably between 30 min and 6 hours, still more preferably between 30 min and 2 hours, most preferably 30 min.

After completion of the reaction, the precipitate is separated in step (e) from the reaction mixture by conventional means, such as filtration.

Subsequently, the obtained gallium-doped phosphocalcic compound may be further purified and/or transformed. In particular, the compound obtained at step (e) may be purified, in particular be washed and dried. The raw product may in particular be washed with ultrapure water and subsequently dried at a suitable temperature, such as 80° C.

The phosphocalcic compound thus obtained has generally a structure similar to calcium deficient apatite (CDA) structure, evidenced by a Ca/P ratio in the 1.44-1.67 range, a $^{31}P$ NMR broad resonance at 2.9 ppm, characteristic X-ray powder diffraction broad lines ($2\theta$=~26° (medium) and ~32° (strong)) and IR absorptions [OH (~3570 $cm^{-1}$) and $PO_4$ (~1040 and 1100 $cm^{-1}$)]. The gallium may be included within the crystal or be present on its surface either as physically sorbed, chemically sorbed or precipitated gallium species.

Gallium-doped phosphocalcic compounds obtainable by the process described above may present in particular a (Ca+Ga)/P molar ratio in the range of 1.3 to 1.67, and a gallium content up to 4.5% by weight.

The gallium-doped phosphocalcic compound obtained may be subsequently calcinated to obtain a galliated compound with a β-TCP-like structure, for example by heating it to a temperature of typically between 800 and 1500° C., more preferably between 900 and 1300° C., most preferably at 1100° C., preferably for a period of time of several hours, especially 3 hours to 5 hours, typically 4 hours.

At last, another process for the manufacture of gallium-doped phosphocalcic compounds relies on a solid/liquid reaction, wherein the calcium deficient apatite (CDA) is suspended in an aqueous gallium solution and the mixture is left to react under controlled pH conditions, preferably under stirring. A preferred pH range for the reaction is a slightly alkaline pH, such as between 8 and 9. The reacted solid is then separated from the reaction mixture by a suitable method, such as centrifugation, and subsequently washed and dried.

The galliated calcium phosphate biomaterials made from the gallium-doped phosphocalcic compounds may then be used as described below.

Methods of Use

Another object of the invention is the use of the galliated calcium phosphate biomaterial according to the invention for dental and medical applications relating in particular to bone repair, augmentation, reconstruction, regeneration, and treatment of bone disease such as osteoporosis.

Additional medical applications include repair of bony defects, repair of bone fractures for spine fusion, prosthetic (hip, knee, shoulder or others) surgery revision, bone augmentation, and bone reconstructions associated with cancer therapy.

The material according to the invention is particularly useful for filling a bony or tooth defect or fracture such as those caused by trauma, osteoporosis, osteolytic tumours, or articular or dental prosthesis surgery.

In particular, the composition may be useful in orthopaedics, such as spine surgery where positioning precisely the CPC graft is critical and more generally in bony environments where pathological bone resorption activity has to be avoided.

Main dental applications are the repair of periodontal defects, sinus augmentation, maxillofacial reconstruction, pulp-capping materials, cleft-palate repair, and as adjuvants to dental implants.

Injectable galliated calcium phosphate cement can be placed to inaccessible parts of the body and is thus particularly well suited for minimally invasive surgery procedures that reduce damage and pain while hastening return to function.

A further object of the invention are thus methods for reconstructive bone surgery and methods of treatment of bone diseases notably due to osteoclastic dysfunctions comprising the introduction into the body of the patient in need thereof, close to the bone site to be treated, of a galliated calcium phosphate biomaterial according to the invention.

According to preferred embodiments of the invention, the introduction is made by injection.

For example, such calcium phosphate cement can be employed in percutaneous vertebroplasty. This consists of a percutaneous puncture method to stabilize and straighten vertebral collapse of the thoracic and lumbar spinal column, most often as a result of osteoporosis.

In the course of osteoporosis, a very painful vertebral collapse can occur in the region of the thoracic (TSC) and lumbar (LSC) spinal column as a result of the reduced load-bearing capacity of the skeletal frame. This results in more or less distinct deformation of the vertebrae, and even in vertebral collapse. Both cases are easily recognizable by X-ray. Even a complete vertebral collapse and distinct deformation of the entire spinal column is possible.

Under local anesthetic, or, if desired, under full narcosis, a thin puncture needle is inserted to the vertebra, e.g. under X-ray guidance. At a certain point of the vertebra (the so-called pedicel), the bone can be punctured by the needle without risk. Afterwards, fluid bone cement is injected into the vertebra via the puncture needle; after the cement hardens, the vertebra is stabilized (vertebroplasty). If the vertebra is severely deformed (e.g. in the case of a wedge-like formation), the collapsed vertebra is straightened before the cement is injected. A balloon is hereby inserted into the vertebra via the puncture needle and inflated with fluid under high pressure. Following a successful straightening, the balloon is removed and the resulting cavity is filled with bone cement (balloon-kyphoplasty). In this case, due to the presence of gallium, the radio-opacity of the implant is increased, thus facilitating performing the surgical operation under radioscopy and an additional advantage is that the metabolism of the implant after implantation can be followed as well.

The invention will be further illustrated in view of the following figures and examples.

using a Philips PW 1830 generator equipped with a vertical PW 1050 (θ/2 θ) goniometer and a PW 1711 Xe detector. The data were acquired using a Ni filtered copper Kα radiation in a step by step mode with: 2θ initial: 10°, 2θ final: 100°, step 2θ=0.03°, time per step: 2.3 seconds.

The atomic coordinates for $Ca_{9.27}Ga_{0.82}(PO_4)_7$ thus obtained are indicated in table 1. From the data obtained, it is apparent that the compound has a β-TCP-type structure wherein one of the 5 calcium sites is gradually replaced by gallium, while a second calcium site empties for charge compensation. The space group is R3c with a=10.322 Å, c=37, 179 Å, α=90°; β=90° and γ=120°.

Figure 1:
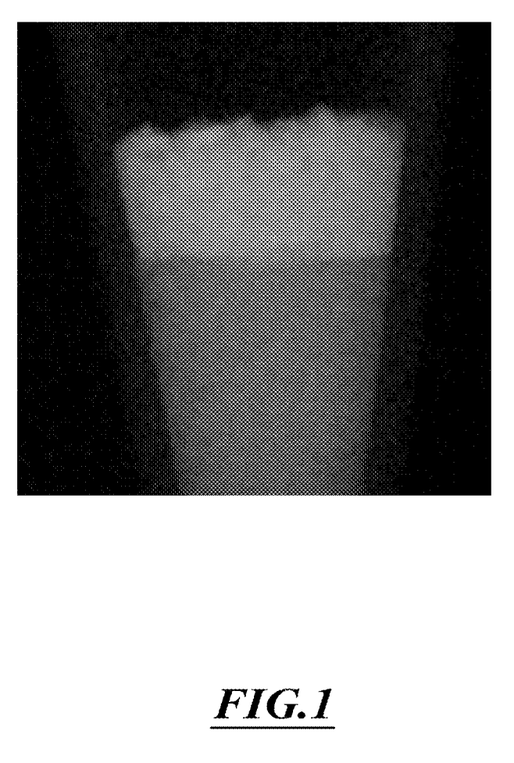
FIG. 1: X-Ray microradiography of a gallium-doped phosphocalcic compound prepared according to example 1 (top) versus TCP without Ga (bottom) showing the higher radio-opacity of compound according to the invention.
Figure 2:
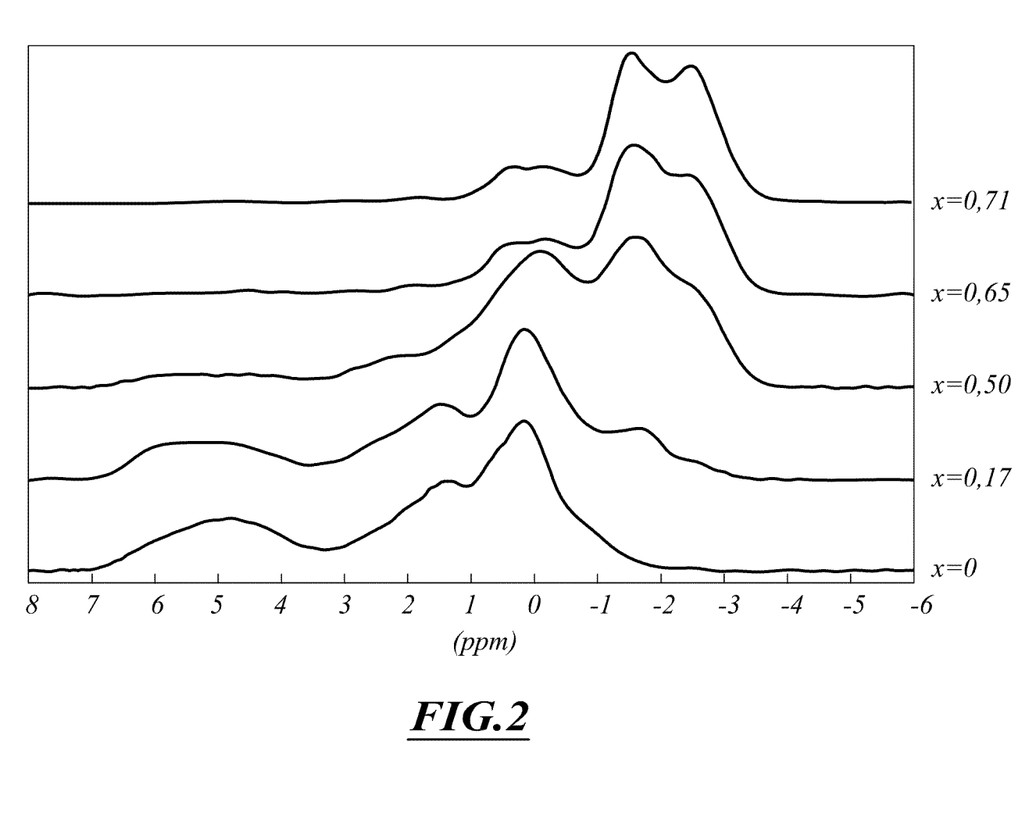
FIG. 2: $^{31}$P MAS NMR spectra of powdered samples of $Ca_{(10.5-1.5x)}Ga_x(PO_4)_7$ for different values of x, recorded at 7.0 T using a 4 mm probehead and $ZrO_2$ rotors.

The $^{31}$P MAS NMR spectra recorded at 7.0 T using a 4 mm probehead and $ZrO_2$ rotors (FIG. 2) were taken from the compounds. The spectra show an upfield shift of the NMR peaks as the number of phosphate sites bound to gallium increases.

Figure 3:
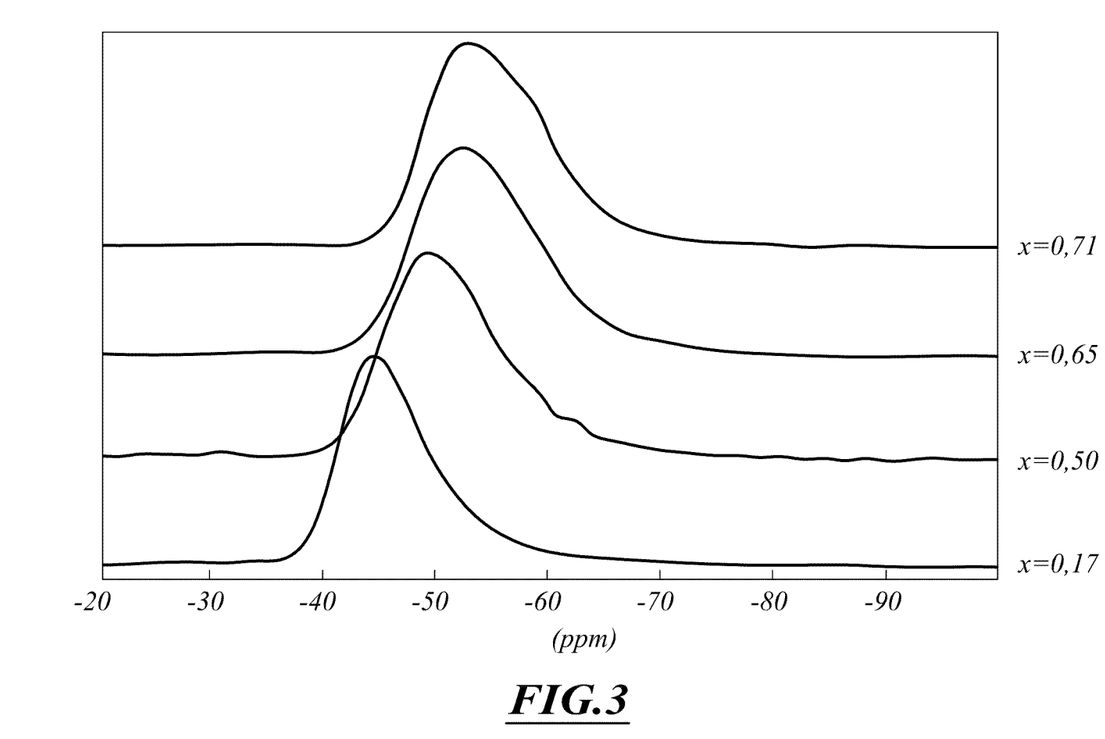
FIG. 3: $^{71}$Ga echo MAS NMR spectra of powdered samples of $Ca_{(10.5-1.5x)}Ga_x(PO_4)_7$ for 0.17<x<0.71, recorded at 17.6 T.

The $^{71}$Ga echo MAS NMR spectra of $Ca_{(10.5-1.5x)}Ga_x(PO_4)_7$ (FIG. 3) recorded at 17.6 T. The spectra show the presence of gallium ions in the compounds, with an isotropic chemical shift characteristic of a $GaO_6$ environment [−38 to −46 ppm], in agreement with the X-ray structure determination.

TABLE 1

Refined atomic coordinates for $Ca_{9.27}Ga_{0.82}(PO_4)_7$

| Atom | Wyckoff Position | Site | Occupancy | x/a | y/b | z/c | U [Å$^2$] |
|---|---|---|---|---|---|---|---|
| Ca1 | 18b | 1 | | 0.7226(5) | 0.8565(7) | 0.1656(2) | 0.0096(6) |
| Ca2 | 18b | 1 | | 0.6215(5) | 0.8243(8) | −0.0348(2) | 0.0096(6) |
| Ca3 | 18b | 1 | | 0.1303(6) | 0.2781(4) | 0.0589(2) | 0.0096(6) |
| Ga | 6a | 3 | 0.817 | 0 | 0 | −0.26632 | 0.0055(14) |
| Ca5 | 6a | 3 | 0.183 | 0 | 0 | −0.26632 | 0.0055(14) |
| Ca4 | 6a | 3 | 0.092 | 0 | 1.00000 | −0.061(2) | 0.0096(6) |
| P1 | 6a | 3 | | 0 | 0 | 0.0000(3) | 0.0068(9) |
| P2 | 18b | 1 | | 0.6828(6) | 0.8580(8) | −0.1303(2) | 0.0068(9) |
| P3 | 18b | 1 | | 0.6553(8) | 0.8476(9) | −0.2359(2) | 0.0068(9) |
| O1 | 6a | 3 | | 0 | 0 | 0.0449(5) | 0.0045(10) |
| O2 | 18b | 1 | | 0.0169(14) | 0.8634(11) | −0.0099(4) | 0.0045(10) |
| O3 | 18b | 1 | | 0.7364(13) | 0.9132(13) | −0.0922(4) | 0.0045(10) |
| O4 | 18b | 1 | | 0.751(2) | 0.7672(18) | −0.1455(4) | 0.0045(10) |
| O5 | 18b | 1 | | 0.726(2) | 0.0002(16) | −0.1529(4) | 0.0045(10) |
| O6 | 18b | 1 | | 0.5058(14) | 0.758(2) | −0.1324(4) | 0.0045(10) |
| O7 | 18b | 1 | | 0.6084(16) | 0.9581(16) | −0.2217(4) | 0.0045(10) |
| O8 | 18b | 1 | | 0.5840(17) | 0.6940(18) | −0.2130(4) | 0.0045(10) |
| O9 | 18b | 1 | | 0.8297(15) | 0.921(2) | −0.2288(4) | 0.0045(10) |
| O10 | 18b | 1 | | 0.6264(12) | 0.8208(16) | 0.7249(4) | 0.0045(10) |

EXAMPLES

Example 1

Preparation of Gallium-Doped Calcium Phosphate by Solid State Reaction

In a mortar, anhydrous calcium phosphate (0.174 mol) was intimately mixed with the quantity of calcium carbonate and gallium oxide calculated such that the (Ca+Ga)/P molar ratio corresponds to the desired x value using the equation below. Calcination of the mixture in a crucible, typically on a 5 gram preparation scale, was performed at 1000° C. for 24 hours (heating rate: 5° C./min, cooling rate 5° C./min).

The structure of the compound was obtained by Rietveld refinement from X-ray powder diffraction patterns, recorded

Example 2

Preparation of Gallium Doped Calcium Phosphate by Coprecipitation

For a product with a (Ca+Ga)/P molar ratio of 1.5, a mixture of 0.444 g gallium nitrate (Aldrich, MW=390) and 2.685 g calcium nitrate tetrahydrate (MW=236) are dissolved in a beaker containing 125 mL of ultrapure water.

The pH of the solution is adjusted in the 9-9.5 range by means of a concentrated solution of ammonia. The reaction mixture is then introduced in a three-neck angled round bottom flask placed in an oil bath and equipped with a dropping funnel. Into the dropping funnel are introduced 1.089 g of diammonium hydrogen phosphate (MW=132) dissolved in 125 mL of ultrapure water. The temperature of the reaction mixture is raised to 50° C. and the solution of diammonium hydrogen phosphate is added dropwise over a 5-10 minutes period. The mixture turns white. The pH is adjusted in the 7.5-8 range by means of a concentrated solution of ammonia (initial time of reaction). After 30 minutes, the heater is stopped and the suspension (pH is neutral) is centrifuged. The main part of the supernatant is removed and the solid residue is washed with 250 mL of ultrapure water, centrifuged and again separated from the main part of the supernatant. After repeating this procedure four times, the final solid is filtered off. The white waxy product is dried in the oven at 80° C. during 24 hours.

Figure 4:
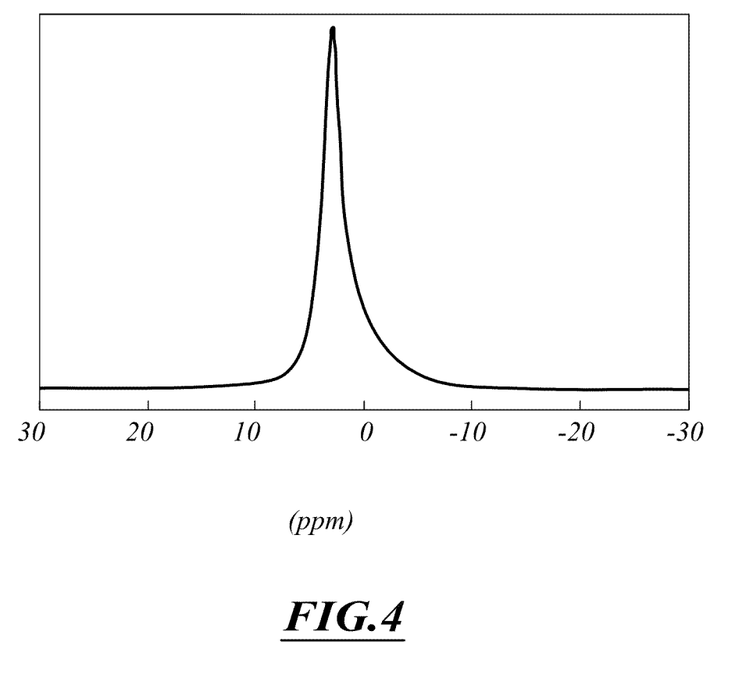
FIG. 4: $^{31}$P MAS NMR spectrum of a powdered sample of the gallium-doped CDA isolated for an initial Ga/P ratio of 0.07, recorded at 7.0 T. After calcination at 1000° C., $Ca_{9.75}Ga_{0.5}(PO_4)_7$ was obtained.

The compounds were characterized by IR spectroscopy [OH (~3570 cm$^{-1}$) and PO$_4$ (~1040 and 1100 cm$^{-1}$)], powder X-ray diffraction [broad lines at 2θ=~26° (medium) and ~32° (strong)] and $^{31}$P MAS NMR spectroscopy [broad resonance at 2.9 ppm] before calcination at 1000° C. (FIG. 4). The corresponding data are characteristic of a calcium deficient apatite.

This was also confirmed by elemental analysis which showed a (Ca+Ga)/P molar ratio in the 1.3-1.5 range and a gallium content up to 4.5% by weight.

After calcination at 1000° C., the resulting compounds correspond to those obtained in example 1 (x=0-0.75), as confirmed by powder X-ray diffraction and solid state $^{31}$P and $^{71}$Ga NMR, indicating a structure close to β-TCP. For large amounts of gallium nitrate (initial Ga/P ratio>about 0.15), the presence of by-products (mainly gallium oxide) mixed with the gallium-doped TCP phase was observed in the calcined compound.

Example 3

Preparation of Gallium Doped CDA by Solid/Liquid Reaction

One liter of a gallium nitrate solution (up to 0.25·10$^{-3}$ mole l$^{-1}$) in ultrapure water was prepared, and the pH was adjusted to 8.4 by addition of a 10 wt % NH$_4$OH solution. 2 g of CDA was suspended in this solution and the pH was again adjusted to 8.4 by addition of a 10 wt % NH$_4$OH solution. The suspension was placed in a tube maintained at room temperature, and was stirred with a rotary stirrer at 16 rpm for 2 days. The suspension was then centrifuged and the most part of the supernatant was removed. The solid residue was filtered off, washed several times with small portions of ultrapure water, and then dried at room temperature. The resulting solid contained up to 0.65 wt % gallium. The compounds were characterized by IR spectroscopy [OH (~3570 cm$^{-1}$) and PO$_4$ (~1040 and 1100 cm$^{-1}$)], powder X-ray diffraction [broad lines at 2θ=~26° (medium) and ~32° (strong)] and $^{31}$P MAS NMR spectroscopy [broad resonance at 2.9 ppm] before calcination at 1000° C. (FIG. 4). The corresponding data are characteristic of a calcium deficient apatite.

Example 4

Preparation of an Apatitic Palliated Calcium Phosphate Cement

Gallium-doped calcium phosphate cements were prepared by mixing ground α-TCP, β-TCP, DCPA and CDA, using gallium doped CDA or β-TCP.

The α-TCP was obtained by calcination of a 2:1 molar mixture of CaHPO$_4$ and CaCO$_3$ at 1350° C. for at least 4 hours, and subsequent rapid cooling at room temperature. The reaction product contained less than 5% of β-TCP.

Gallium-doped β-TCP was prepared according to example 1. Gallium-doped CDA was synthesized according to example 2.

The main component of the cement mixtures was α-TCP, which was ground so that about 50% of the solid had a particle size between 0.1 and 8 μm, about 25% between 8 and 25 μm and a further 25% between 25 and 80 μm.

The composition of the cement mixtures are indicated in table 2 below.

TABLE 2

Composition of apatitic galliated calcium phosphate cements

| Composition of the solid phase | α-TCP [weight %] | β-TCP [weight %] | DCPA$_4$ [weight %] | CDA [weight %] |
|---|---|---|---|---|
| Control | 55 | 20 Ca$_{10.5}$(PO$_4$)$_7$ | 20 | 5 |
| Sample 1 | 55 | 20 Ca$_{9.5}$Ga$_{0.82}$(PO$_4$)$_7$ | 20 | 5 |
| Sample 2 | 55 | 20 Ca$_{9.375}$Ga$_{0.75}$(PO$_4$)$_7$ | 20 | 5 |
| Sample 3 | 55 | 20 Ca$_{9.75}$Ga$_{0.5}$(PO$_4$)$_7$ | 20 | 5 |
| Sample 4 | 55 | 20 Ca$_{10.5}$(PO$_4$)$_7$ | 20 | 5 (doped with 4.5 wt % Ga) |

Cement pastes were then prepared from the cement powders using as the liquid phase a 2.5 wt % solution of Na$_2$HPO$_4$ in distilled water. The liquid/powder ratio used was 0.35 ml/g.

The cements thus prepared were characterized in terms of initial setting times, compressive strength and X-ray diffraction patterns.

The initial setting times were determined at room temperature (20±1° C.) according to the ASTM standard by means of Gilmore needles. The results are indicated in table 3 below.

The compressive strength was determined using a Texture analyzer. First, cement cylinders with a 12 mm height and a 6 mm diameter, prepared in Teflon molds. The cylinders were then soaked during 24 hours in Ringer's solution at 37° C. prior to determination of the compressive strength with a Texture Analyzer at a compression rate of 1 mm/min. The results are indicated in table 3 below.

The hardened cement materials were further studied using X-ray diffraction. Despite the presence of gallium-doped β-TCP or CDA, the main final product formed was found to be a calcium deficient hydroxyapatite resulting from the transformation of α-TCP.

TABLE 3

Setting times and compressive strengths of cements of example 4

| Sample | Initial setting time (min) | Compressive strength (MPa) |
|---|---|---|
| Control | 32 ± 2 | 29.33 ± 2 |
| Sample 1 | 33 ± 1 | 30.47 ± 2 |

TABLE 3-continued

Setting times and compressive strengths of cements of example 4

| Sample | Initial setting time (min) | Compressive strength (MPa) |
|---|---|---|
| Sample 2 | 30 ± 1 | 31.33 ± 3 |
| Sample 3 | 32 ± 2 | 31.51 ± 2 |
| Sample 4 | 36 ± 1 | 31.25 ± 1 |

The results show that the setting times and compressive strengths are not affected by the incorporation of gallium, when introduced via gallium-doped β-TCP or CDA. The obtained data further indicate that the materials obtained are suitable for a clinical use.

Example 5

Preparation of an Apatitic Galliated Calcium Phosphate Cement Comprising MCPM and HPMC Gallium-doped calcium phosphate cements were prepared by mixing ground α-TCP, gallium doped β-TCP, DCPD, CDA, MCPM and HPMC.

The α-TCP was obtained by calcination of a 2:1 molar mixture of $CaHPO_4$ and $CaCO_3$ at 1350° C. for at least 4 hours, and subsequent rapid cooling to room temperature. The reaction product contained less than 5% of β-TCP.

Gallium-doped β-TCP was prepared according to example 1. The main component of the cement mixtures was α-TCP, which was ground so that about 50% of the solid had a particle size between 0.1 and 8 μm, about 25% between 8 and 25 μm and a further 25% between 25 and 80 μm.

The composition of the cement mixtures prepared is indicated in table 4 below.

TABLE 4

Composition of apatitic galliated calcium phosphate cements

| Composition of the solid phase | α-TCP [weight %] | β-TCP [weight %] | DCPD [weight %] | CDA [weight %] | MCPM [weight %] | HPMC [weight %] |
|---|---|---|---|---|---|---|
| Control | 66.3 | 15<br>$Ca_{10.5}(PO_4)_7$ | 4.25 | 8.5 | 4.25 | 1.7 |
| Sample 5 | 66.3 | 15<br>$Ca_{9.75}Ga_{0.5}(PO_4)_7$ | 4.25 | 8.5 | 4.25 | 1.7 |

Cement pastes were then prepared from the cement powders using as the liquid phase a 5 wt % solution of $Na_2HPO_4$ in distilled water. The liquid/powder ratio used was 0.50 ml/g.

The cements thus prepared were characterized in terms of initial setting times, compressive strength and X-ray diffraction patterns.

The initial setting times were determined at room temperature (37±1° C.) according to the ASTM standard by means of Gilmore needles and a thermostated cell. The results are indicated in table 5 below.

The compressive strength was determined using a Texture analyzer. First, cement cylinders with a 12 mm height and a 6 mm diameter were prepared in Teflon molds. The cylinders were then soaked during 24 hours in Ringer's solution at 37° C. prior to determination of the compressive strength with a Texture Analyzer at a compression rate of 1 mm/min. The results are indicated in table 5 below.

The hardened cement materials were further studied using X-ray diffraction. Despite the presence of gallium-doped β-TCP, the main final product formed was found to be a calcium deficient hydroxyapatite resulting from the transformation of α-TCP.

TABLE 5

Setting times and compressive strengths

| Sample | Initial setting time (min) | Compressive strength (MPa) |
|---|---|---|
| Control | 15 ± 2 | 6.5 ± 2 |
| Sample 5 | 15 ± 2 | 6.7 ± 2 |

The results show that the setting times and compressive strengths are not affected by the incorporation of gallium, when introduced via gallium-doped β-TCP.

After a setting time of 48 hours, Control and Sample 5 (table 5) present the same α-TCP to CDA conversion (%) rate (66±3). The obtained data further indicate that the materials obtained are suitable for a clinical use.

Example 6

Preparation of an Apatitic Palliated Calcium Phosphate Cement

Gallium-doped calcium phosphate cements were prepared by mixing ground α-TCP, gallium doped CDA, DCPD, MCPM and HPMC.

The α-TCP was obtained by calcination of a 2:1 molar mixture of $CaHPO_4$ and $CaCO_3$ at 1350° C. for at least 4 hours, and subsequent rapid cooling to room temperature. The reaction product contained less than 5% of β-TCP and Gallium-doped CDA was synthesized according to example 3.

The main component of the cement mixtures was α-TCP, which was ground so that about 50% of the solid had a particle size between 0.1 and 8 μm, about 25% between 8 and 25 μm and a further 25% between 25 and 80 μm.

The composition of the cement mixtures are indicated in table 6 below.

TABLE 6

Composition of apatitic galliated calcium phosphate cements

| Composition of the solid phase | α-TCP [weight %] | CDA [weight %] | DCPD [weight %] | MCPM [weight %] | HPMC [weight %] |
|---|---|---|---|---|---|
| Control | 78 | 10 | 5 | 5 | 2 |
| Sample 6 | 78 | 10 (doped with 4.5 wt % Ga according to exemple 2) | 5 | 5 | 2 |
| Sample 7 | 78 | 10 (doped with 0.27 wt % Ga according to exemple 3) | 5 | 5 | 2 |

Cement pastes were then prepared from the cement powders using as the liquid phase a 5 wt % solution of $Na_2HPO_4$ in distilled water. The liquid/powder ratio used was 0.50 ml/g.

The cements thus prepared were characterized in terms of initial setting times, compressive strength and X-ray diffraction patterns.

The initial setting times were determined at room temperature (37±1° C.) according to the ASTM standard by means of Gilmore needles and a thermostated cell. The results are indicated in table 7 below.

The compressive strength was determined using a Texture analyzer. First, cement cylinders with a 12 mm height and a 6 mm diameter were prepared in Teflon molds. The cylinders were then soaked during 24 hours in Ringer's solution at 37° C. prior to determination of the compressive strength with a Texture Analyzer at a compression rate of 1 mm/min. The results are indicated in table 7 below.

The hardened cement materials were further studied using X-ray diffraction. Despite the presence of gallium-doped CDA, the main final product formed was found to be a calcium deficient hydroxyapatite resulting from the transformation of α-TCP.

TABLE 7

Setting times and compressive strengths of cements of example 6

| Sample | Initial setting time (min) | Compressive strength (MPa) |
|---|---|---|
| Control | 14 ± 2 | 9.4 ± 2 |
| Sample 6 | 15 ± 2 | 7.2 ± 2 |
| Sample 7 | 14 ± 2 | 8.3 ± 2 |

The results show that the setting times and compressive strengths are not affected by the incorporation of gallium, when introduced via gallium-doped CDA. The obtained data further indicate that the materials obtained are suitable for a clinical use.

REFERENCES

Albee F H *Ann. Surg.* (1920) 71, 32-39
Bernstein L. R., *Pharmacological Reviews* 1998, 50, (4), 665-682.
Blumenthal N C and Cosma V (1989) Bull Hosp Jt Dis Orthop Inst 49: 192-204
Bockman R S and Bosco B (1994), Semin Arthritis Rheum 23: 268-269
Bockman R S et al. (1989), *J Bone Miner Res* 4: S167.
Bockman R S et al. (1995) J Clin Endocrinol Metab 80:595-602.
Brown W E and Chow L C (1983) J. Dent. Res. 62: 672.
Dickens B. et al. (1974) J Solid State Chem 10, 232
Donnelly R., et al. Calcif Tissue Int., 1993. 53(6): p. 400-10
Donnelly R. and Boskey A. (1989), Calcif Tissue Int 44: 138-142
Dudley H C and Maddox G E (1949) *J Pharmacol Exp Ther* 96: 224-227
Golubev et al. Neorganicheskoi khimii 35, (12): 3037-3041, December 1990.
Jarcho M (1986) Dental Clinics of North America 30(1), 25-47
Korbas et al. J Biol Inorg Chem (2004) 9:67-76.
LeGeros et al, J Dent Res 61, Spec Iss:343, 1982
Mathew M. et al. (1977) Acta Crystallogr B33, 1325.
Nelson B et al. J Nucl Med (1972) 13: 92-100
Nery E B et Al., *J. Periodontol.* 1975, 46, 328-347
Pompe, W., et al., Materials Science and Engineering 2003 A362: 40-60.
Ray R D and Ward A A *Surg. Form.* 1951, 429-434
Valappil S P et al Acta Biomaterialia (2008), doi: 10.1016/j.actbio.2008.09.019
Warrell R P Jr (1995) in Handbook of Metal-Ligand Interactions in Biological Fluids, Bioinorganic Medicine (Berthon G ed) vol 2, pp 1253-1265, Marcel Dekker, New York.
Warrell R P Jr et al. (1987) J Clin Oncol 5: 292-298.
Warrell R P Jr and Bockman R S (1989) in Important Advances in Oncology 1989 (DeVita V T, Hellman S and Rosenberg S A eds) pp 205-220, J. B. Lippincott, Philadelphia.
Warrell R P et al. (1984) J Clin Invest 73: 1487-1490.
Warrell R P Jr, et al. (1985) Cancer Treat Rep 69: 653-655.
Warrell R P Jr et al., (1993) J Clin Oncol 11: 2443-2450.
Yang, et al., The design of scaffolds for use in tissue engineering. Part I. Traditional factors, Tissue Eng. 2001 7(6): 679-689.
Yashima M. et al. (2003) J Solid State Chem 175, 272.

We claim:

1. A galliated calcium-phosphate biomaterial comprising a compound selected from a gallium-doped phosphocalcic compound of formula (1):

$$Ca_{(10.5-1.5x)}Ga_x(PO_4)_7 \qquad (1)$$

wherein 0≤x≤1 and
characterized in that it crystallizes at least partially in the space group R3c with cell parameters varying in the following range, as a function of the Ga content: a=10.31-10.44 Å, c=37.15-37.5 Å, α=90°; β=90° and γ=120° and/or
characterized by a Ca/P ratio comprised between 1.44 and 1.67 and an X-ray powder diffraction broad lines at 2θ~26° (medium) and ~32° (strong),
and hydrates thereof.

2. The galliated calcium phosphate biomaterial according to claim 1, wherein in formula (I) $0<x\leq0.85$.

3. The galliated calcium phosphate biomaterial according to claim 1, wherein the gallium-doped phosphocalcic compound of formula (I) is selected from the group consisting of $Ca_{10.125}Ga_{0.25}(PO_4)_7$; $Ca_{9.75}Ga_{0.5}(PO_4)_7$; $Ca_{9.375}Ga_{0.75}(PO_4)_7$; and $Ca_{9.5}Ga_{0.82}(PO_4)_7$.

4. The galliated calcium-phosphate biomaterial comprising a gallium-doped phosphocalcic compound according to claim 1, obtainable by a solid-state process comprising the steps of:
   (a) contacting calcium phosphate with calcium carbonate in presence of a suitable quantity of a gallium compound;
   (b) sintering the mixture to form a gallium-doped phosphocalcic compound; and
   (c) recovering the gallium-doped phosphocalcic compound and having a gallium content of up to 5.3% by weight.

5. A galliated calcium-phosphate biomaterial comprising a gallium-doped phosphocalcic compound according to claim 1, obtainable by a process comprising the steps consisting of:
   (a) preparing an aqueous solution containing a calcium compound and an appropriate quantity of a gallium compound;
   (b) adjusting the pH of the solution obtained in step (a) to a value of 8.5 to 12, if necessary;
   (c) adding to said solution an appropriate quantity of a phosphate compound;
   (d) precipitating a gallium-doped phosphocalcic compound by adjusting the pH of said solution to a value of 7.0 to 12; and
   (e) separating the precipitated gallium-doped phosphocalcic compound from the solution and having a (Ca+Ga)/P molar ratio in the range of 1.3-1.67, and a gallium content up to 4.5% by weight.

6. A galliated calcium-phosphate biomaterial comprising a gallium-doped phosphocalcic compound according to claim 1, obtainable by a solid/liquid process comprising the steps of:
   (a) suspending calcium phosphate in an aqueous gallium solution, the pH of which is adjusted to a value of 8 to 9;
   (b) stirring the resulting suspension at room temperature; and
   (c) separating the gallium-doped phosphocalcic compound from the solution and having a (Ca+Ga)/P molar ratio in the range of 1.3-1.67 and a gallium content up to 0.65% by weight.

7. The galliated calcium phosphate biomaterial according to claim 5, comprising a phosphocalcic compound characterized by a Ca/P ratio comprised between 1.44 and 1.67 and an X-ray powder diffraction broad lines at $2\theta\sim26°$ (medium) and $\sim32°$ (strong).

8. The galliated calcium phosphate biomaterial according to claim 6, comprising a phosphocalcic compound characterized by a Ca/P ratio comprised between 1.44 and 1.67 and an X-ray powder diffraction broad lines at $2\theta\sim26°$ (medium) and $\sim32°$ (strong).

9. The galliated calcium-phosphate biomaterial according to claim 1, wherein the material is self-setting.

10. The galliated calcium-phosphate biomaterial according to claim 1, further comprising a polymer.

11. A process for the manufacture of a galliated calcium phosphate biomaterial according to claim 9, comprising the steps of:
    providing an appropriate amount of $TCP(Ca_3(PO_4)_2)$;
    mixing the TCP with appropriate amounts of one or more gallium doped phosphocalcic compounds and optionally other additives; and
    grinding of the components to form a solid phase of a calcium phosphate cement.

12. An implant comprising the galliated calcium phosphate biomaterial according to claim 1.

13. A process for the manufacture of the implant according to claim 12 comprising the step of:
    (i) mixing the self-setting galliated calcium phosphate biomaterial according to claim 9 with an appropriate amount of an aqueous liquid phase to obtain a cement paste; and
    (ii) forming the cement paste into an implant.

14. A kit comprising the galliated calcium phosphate biomaterial according to claim 1 in combination with a fluid component.

15. A method for filling a bony or tooth defect comprises using the galliated calcium phosphate biomaterial according claim 1.

* * * * *